(12) United States Patent
Borovik et al.

(10) Patent No.: US 7,022,864 B2
(45) Date of Patent: Apr. 4, 2006

(54) ETHYLENEOXIDE-SILANE AND BRIDGED SILANE PRECURSORS FOR FORMING LOW K FILMS

(75) Inventors: Alexander S. Borovik, West Hartford, CT (US); Chongying Xu, New Milford, CT (US); Thomas H. Baum, New Fairfield, CT (US); Steven Bilodeau, Oxford, CT (US); Jeffrey F. Roeder, Brookfield, CT (US); Abigail Ebbing, Danbury, CT (US); Daniel Vestyck, Danbury, CT (US)

(73) Assignee: Advanced Technology Materials, Inc., Danbury, CT (US)

( * ) Notice: Subject to any disclaimer, the term of this patent is extended or adjusted under 35 U.S.C. 154(b) by 147 days.

(21) Appl. No.: 10/619,785

(22) Filed: Jul. 15, 2003

(65) Prior Publication Data

US 2005/0013936 A1  Jan. 20, 2005

(51) Int. Cl.
 *C07F 7/18* (2006.01)
 *B05D 5/12* (2006.01)
 *H05H 1/42* (2006.01)

(52) U.S. Cl. ............... 549/215; 106/287.16; 427/70; 427/578; 427/585

(58) Field of Classification Search ........... 549/215; 106/287.16; 427/70, 578, 585
See application file for complete search history.

(56) References Cited

U.S. PATENT DOCUMENTS 6,583,048 B1  6/2003 Vincent et al.
6,846,515 B1  1/2005 Vrtis et al.

OTHER PUBLICATIONS

R. N. 18191-70-3, Brodsky et al, Chem. Abstr. 136:142449 (2001).*
R.N. 266337-39-7,Kibayashi et al, Chem. Abstr. 132:322978 (2000).*
R.N. 17611-73-3, Dubrovin et al,Chem. Abstr. 106:224291 (1987).*
R.N. 30423-45-1, Tsuruta et al, Chem. Abstr. 68:87648 (1968).*
R.N. 23820-01-1 and 33979-86-1, Chem.. Abstr. 75:140971 (1971).*
R.N. 415708, Chem. Abstr. 136:326874 (2002).*
R.N. 60484-85-7, Chem.Abstr. 136:37651 (2001).*
Behrendt et al, Chem. Abstr. 108:206543 (1988).*

* cited by examiner

*Primary Examiner*—Bernard Dentz
(74) *Attorney, Agent, or Firm*—Steven J. Hultquist; Intellectual Property/Technology Law

(57) ABSTRACT

An organosilicon precursor for vapor deposition, e.g., low pressure (<100 Torr), plasma-enhanced chemical vapor deposition (PECVD) of a low k, high strength dielectric film, wherein the precursor includes at least one of:
 (i) silicon-pendant oxiranyl functionality; and
 (ii) a disilyl moiety of the formula

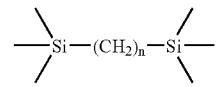

wherein x is an integer having a value of from 0 to 4 inclusive. These precursors are useful for the formation of dielectric films having dielectric constants on the order of ~3 and less, and a hardness exceeding ~1 GigaPascals.

29 Claims, 2 Drawing Sheets

ETHYLENEOXIDE-SILANE AND BRIDGED SILANE PRECURSORS FOR FORMING LOW K FILMS

BACKGROUND OF THE INVENTION

1. Field of the Invention

The present invention relates to low dielectric constant films, and to precursors and methods useful in making such films.

2. Description of the Related Art

As semiconductor devices are scaled to higher processor speeds and smaller, denser structures, there is an increasing need to reduce resistance-capacitance (RC) delays present in interconnect wiring. Since the dielectric constant k is proportional to capacitance (C), scaling relationships require reductions in k values of the dielectric material. In addition to the requirement of low k values, reliability issues require that the dielectric material have a high degree of mechanical strength. Currently available dielectric films have low mechanical strength as k values decrease.

Among the various materials that are currently available for forming low k films, 1,3,5,7-tetramethylcyclotetrasiloxane (TMCTS) is a widely studied precursor for deposition of low k thin films used as interlayer dielectrics in integrated circuitry. Dielectric films formed from TMCTS typically have k values in a range of from about 2.6 to about 3.0, but lack sufficient hardness for large-scale integration. For next generation very large-scale integration (VLSI) devices, dielectrics will be required that have a dielectric constant k below 2.5 with hardness greater than about 1 gigaPascal (gPa).

Accordingly, the art continues to seek improvements in dielectric materials, in the quest for dielectrics having both high mechanical strength and low k value.

SUMMARY OF THE INVENTION

The present invention relates generally to low dielectric constant films, and to precursors and methods useful in making such films, e.g., for the manufacture of semiconductor devices and products.

In one aspect, the invention relates to an organosilicon precursor for vapor deposition, e.g., low pressure (<100 Torr), plasma-enhanced chemical vapor deposition (PECVD) of a low k, high strength dielectric film, wherein the precursor comprises at least one of:

(i) silicon-pendant oxiranyl functionality; and
(ii) a disilyl moiety of the formula

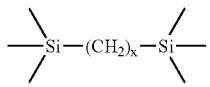

wherein x is an integer having a value of from 0 to 4 inclusive.

In another aspect, the invention relates to an organosilicon precursor composition for vapor deposition of a low k, high strength dielectric film, wherein the composition comprises:

(A) an organosilicon precursor comprising at least one of:
(i) silicon-pendant oxiranyl functionality; and
(ii) a disilyl moiety of the formula

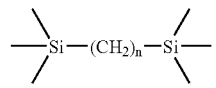

wherein x is an integer having a value of from 0 to 4 inclusive; and
(B) a porogen.

Another aspect of the invention relates to a method of forming an oxiranylsilane compound of formula (I):

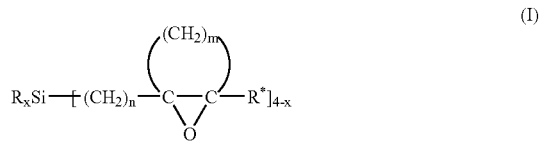

wherein:
m is an integer having a value of 0 to 6, inclusive;
n is 0 or 1;
x is an integer having a value of 0 to 3, inclusive; and
each R and R* can be the same as or different from one another and each is independently selected from the group consisting of H, $C_1$–$C_8$ alkyl, $C_1$–$C_8$ fluoroalkyl, $C_1$–$C_8$ alkoxy, $C_6$–$C_{10}$ cycloalkyl, $C_6$–$C_{10}$ aryl, $C_6$–$C_{10}$ fluoroaryl, $C_2$–$C_6$ vinyl, and $C_3$–$C_6$ allyl, such method comprising oxidizing a corresponding vinylsilane or allylsilane compound.

In one preferred aspect, the oxiranylsilane compound has the formula (II) set out below:

wherein:
each of $R_1$, $R_2$ and $R_3$ can be the same as or different from one another and each is independently selected from the group consisting of H, $C_1$–$C_8$ alkyl, $C_1$–$C_8$ fluoroalkyl, $C_1$–$C_8$ alkoxy, $C_6$–$C_{10}$ cycloalkyl, $C_6$–$C_{10}$ aryl, $C_6$–$C_{10}$ fluoroaryl, $C_2$–$C_6$ vinyl, and $C_3$–$C_6$ allyl; and
n is 0 or 1;

with the proviso that if n=1, then one of $R_1$, $R_2$ and $R_3$ alternatively can be an oxiranyl functionality:

(sometimes hereinafter referred to as ethyleneoxide functionality).

Yet another aspect of the invention relates to a method of synthesizing a bridged disilane compound of formula (III):

$$R^4R^5R^6Si—(CH_2)_y—SiR^7R^8R^9 \qquad (III)$$

wherein:
each of $R^4$, $R^5$, $R^6$, $R^7$, $R^8$ and $R^9$ can be the same as or different from one another and each is independently selected from the group consisting of H, $C_1$–$C_8$ alkyl, $C_1$–$C_8$ fluoroalkyl, $C_1$–$C_8$ alkoxyl, $C_6$–$C_{10}$ cycloalkyl, $C_6$–$C_{10}$ aryl, $C_6$–$C_{10}$ fluoroaryl, $C_2$–$C_6$ vinyl, $C_3$–$C_6$ allyl, and oxiranylalkylene of formula (IV)

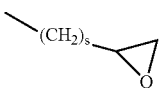

(IV)

wherein s is 0 or 1; and
y is an integer having a value of from 0 to 4 inclusive, such method comprising derivatization of a corresponding bridged chlorosilane.

In a further aspect, the invention relates to a method of forming a low k, high strength dielectric film on a substrate, comprising vapor depositing said film on the substrate from a precursor comprising at least one of:
(i) silicon-pendant oxiranyl functionality; and
(ii) a disilyl moiety of the formula

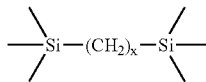

wherein x is an integer having a value of from 0 to 4 inclusive.

Other aspects, features and advantages of the invention will be more fully apparent from the ensuing disclosure and appended claims.

DETAILED DESCRIPTION OF THE INVENTION AND PREFERRED EMBODIMENTS THEREOF

Figure 1:
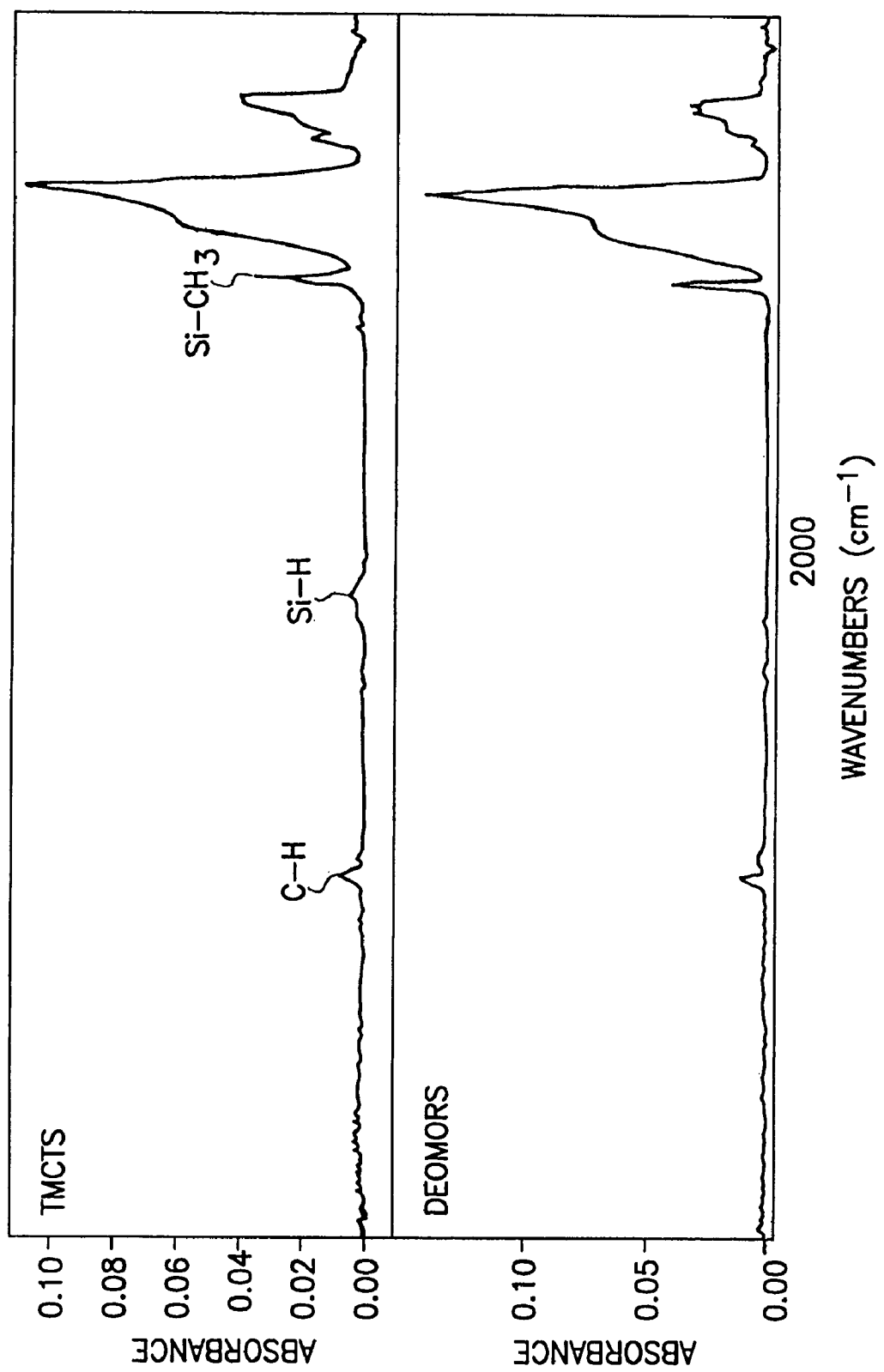
FIG. 1 is a graph of FTIR transmission spectra of a film deposited from TMCTS and a film deposited from Me(EtO$_2$)SiCHCH$_2$O under low oxygen activity deposition conditions.

The present invention contemplates a new class of precursor compounds that are useful in forming low k films having superior mechanical strength characteristics.

The precursor compounds of the invention in a first general category are organosilicon source reagents including silicon-pendant oxiranyl functionality. The organosilicon source reagents include monosilicon-containing compounds as well as polysilicon-containing compounds, e.g., disilanes, disilylalkyl compounds, disiloxanes and cyclosiloxanes. The number of oxiranyl functional groups in the molecule can be selectively adjusted along with other R and OR groups to optimize the behavior of the precursor molecule for a specific film-forming application, e.g., a low-pressure plasma chemical vapor deposition (CVD) process, and the molecule can include H groups in combination with oxira-nyl, methyl, methoxide, and other functionality. Cross-linked silyl structures (having an Si—C—Si moiety) can also be employed in the organosilicon precursors of the invention.

One general class of compounds of the invention has the formula (I):

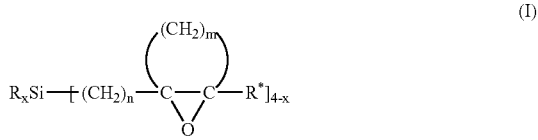

(I)

wherein:
m is an integer having a value of 0 to 6, inclusive;
x is an integer having a value of 0 to 3, inclusive; and
each R and R* can be the same as or different from one another and each is independently selected from the group consisting of H, $C_1$–$C_8$ alkyl, $C_1$–$C_8$ fluoroalkyl, $C_1$–$C_8$ alkoxy, $C_6$–$C_{10}$ cycloalkyl, $C_6$–$C_{10}$ aryl, $C_6$–$C_{10}$ fluoroaryl, $C_2$–$C_6$ vinyl, and $C_3$–$C_6$ allyl.

Within the foregoing general formula (I), one sub-class of oxiranylsilane compounds of the invention has the formula (II):

(II)

wherein:
each of $R_1$, $R_2$ and $R_3$ can be the same as or different from one another and each is independently selected from the group consisting of H, $C_1$–$C_8$ alkyl, $C_1$–$C_8$ fluoroalkyl, $C_1$–$C_8$ alkoxy, $C_6$–$C_{10}$ cycloalkyl, $C_6$–$C_{10}$ aryl, $C_6$–$C_{10}$ fluoroaryl, $C_2$–$C_6$ vinyl, and $C_3$–$C_6$ allyl; and
n is 0 or 1;

with the proviso that if n=1, then one of $R_1$, $R_2$ and $R_3$ alternatively can be

an oxiranyl functionality.

Within the foregoing general formula (I), another sub-class of silyloxirane compounds of the invention has the formula (V):

(V)

wherein:
each of $R_1$, $R_2$ and $R_3$ is independently selected from the group consisting of H, $C_1$–$C_8$ alkyl, $C_1$–$C_8$ fluoroalkyl, $C_1$–$C_8$ alkoxy, $C_6$–$C_{10}$ cycloalkyl, $C_6$–$C_{10}$ aryl, $C_6$–$C_{10}$ fluoroaryl, $C_2$–$C_6$ vinyl, and $C_3$–$C_6$ allyl.

Yet another sub-class of silyloxirane compounds within the general formula set out below has the formula (VI):

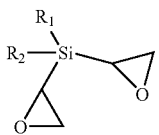

(VI)

wherein:
each of $R_1$ and $R_2$ is independently selected from the group consisting of H, $C_1$–$C_8$ alkyl, $C_1$–$C_8$ fluoroalkyl, $C_1$–$C_8$ alkoxy, $C_6$–$C_{10}$ cycloalkyl, $C_6$–$C_{10}$ aryl, $C_6$–$C_{10}$ fluoroaryl, $C_2$–$C_6$ vinyl, and $C_3$–$C_6$ allyl.

A further sub-class of silyloxirane compounds within the general formula (I) has the formula (VII):

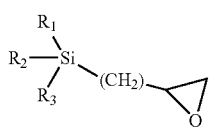

(VII)

wherein:
each of $R_1$, $R_2$ and $R_3$ is independently selected from the group consisting of H, $C_1$–$C_8$ alkyl, $C_1$–$C_8$ fluoroalkyl, $C_1$–$C_8$ alkoxy, $C_6$–$C_{10}$ cycloalkyl, $C_6$–$C_{10}$ aryl, $C_6$–$C_{10}$ fluoroaryl, $C_2$–$C_6$ vinyl, and $C_3$–$C_6$ allyl.

A further sub-class of compounds within the scope of broad formula (I) comprises compounds of the formula (VIII) set out below:

$$(R_1)(R_2)Si\!-\![(CH_2)_n\!-\!\underset{\underset{O}{\vee}}{C}\!-\!\underset{\underset{}{}}{C}\overset{(CH_2)_m}{\overgroup{\phantom{XX}}}\!-\!R^*]_2$$

(VIII)

wherein:
m is an integer having a value of from 0 to 6 inclusive;
n is 0 or 1;
each $R_1$, $R_2$ and $R^*$ can be the same as or different from one another and each is independently selected from the group consisting of H, $C_1$–$C_8$ alkyl, $C_1$–$C_8$ fluoroalkyl, $C_1$–$C_8$ alkoxy, $C_6$–$C_{10}$ cycloalkyl, $C_6$–$C_{10}$ aryl, $C_6$–$C_{10}$ fluoroaryl, $C_2$–$C_6$ vinyl, and $C_3$–$C_6$ allyl.

A further sub-class of oxiranyl compounds of the invention has the formula (IX):

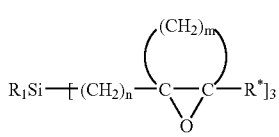

(IX)

wherein:
m is an integer having a value of from 0 to 6 inclusive;
n is 0 or 1;

each of $R_1$ and $R^*$ can be the same as or different from one another and each is independently selected from the group consisting of H, $C_1$–$C_8$ alkyl, $C_1$–$C_8$ fluoroalkyl, $C_1$–$C_8$ alkoxy, $C_6$–$C_{10}$ cycloalkyl, $C_6$–$C_{10}$ aryl, $C_6$–$C_{10}$ fluoroaryl, $C_2$–$C_6$ vinyl, and $C_3$–$C_6$ allyl.

Illustrative compounds within the broad scope of the present invention include the compounds set out below.

Formula (A), Me(EtO)$_2$SiCHCH$_2$O:

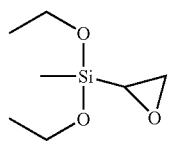

Formula (B), Me(MeO)$_2$Si CH$_2$CHCH$_2$O:

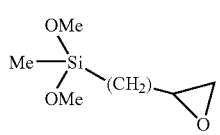

Formula (C), Me$_2$Si(CHCH$_2$O)$_2$:

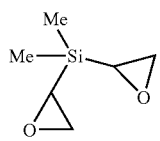

wherein Me is methyl.

The ethyleneoxide-substituted silane compounds of the invention are useful precursors for the formation of low k films having dielectric constant below 2.5, by deposition methods such as plasma-enhanced chemical vapor deposition (PECVD). The ethyleneoxide moiety in the precursor molecule provides a functionality with a weak carbon-oxygen bond. Under mild plasma conditions, this bond breaks first and by absorbing the plasma energy prevents the breakage of other silicon-carbon bonds in the precursor molecule. The resulting incorporation of carbon in the deposited films provides lowered k values. The formation of oxygen and carbon radicals during the PECVD film-forming process also facilitates cross-linking within the film to produce films of superior hardness.

The ethyleneoxide-substituted silane precursor compounds of the invention are readily synthesized by oxidation of either vinyl or allyl groups on correspondingly functionalized silane compounds. Useful oxidizing agents for such purpose include meta-Cl($C_6H_4$)C(O)OOH, denoted m-CPBA, $^t$BuOOH, wherein $^t$Bu is tertiary butyl, and Me$_3$SiOOSiMe$_3$ wherein Me is methyl, as well as other oxidants having sufficient oxidizing strength and inertness in relation to Si—OR fragments. The reaction can be run in a suitable non-flammable solvent medium, e.g., using a solvent such as dichloromethane (CH$_2$Cl$_2$), chloroform (CHCl$_3$), etc., which provides a safe environment for the strong oxidizing agent.

An illustrative example is the synthesis of Me(EtO)$_2$SiCHCH$_2$O, which is obtained in 50% yield according to Reaction (1) below.

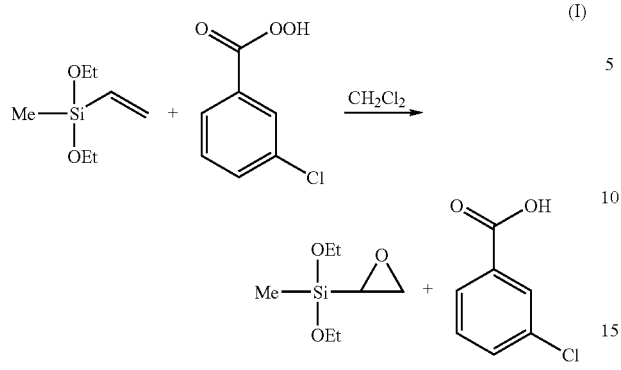

(I)

Another illustrative example is the synthesis of Me(MeO)$_2$SiCH$_2$CHCH$_2$O, which is obtained in almost quantitative yield according to Reaction (2) below.

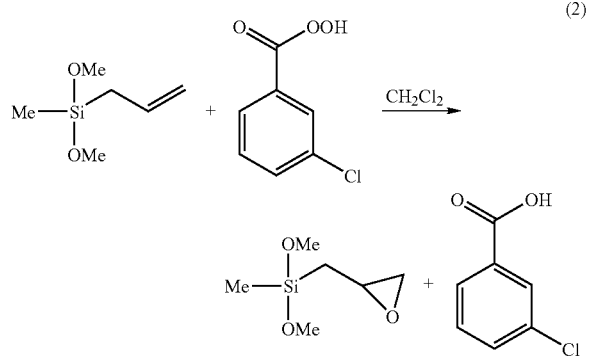

(2)

Reaction (2) involving the allylsilane analog was much faster compared to Reaction (1) involving the corresponding vinyl compound.

Me(EtO)$_2$SiCHCH$_2$O was employed as a precursor for PECVD formation of low k films, and yielded films having a k value of 3.1 and a hardness of 2.3 GPa.

Very low k value films can be obtained using the dioxiranylsilane compounds of formula (III) above, such as Me$_2$Si(CHCH$_2$O)$_2$, which can be synthesized according to Reaction (3) below.

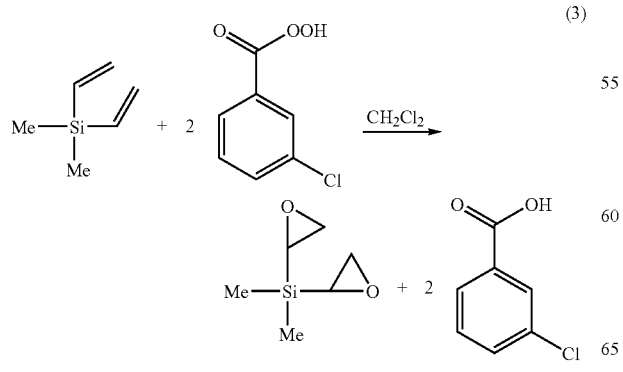

(3)

The precursor compounds of the invention in a second general category are bridged silane source reagents of the formula (III):

$$R^4R^5R^6Si-(CH_2)_y-SiR^7R^8R^9 \qquad (III)$$

wherein:
each of $R^4$, $R^5$, $R^6$, $R^7$, $R^8$ and $R^9$ can be the same as or different from one another and each is independently selected from the group consisting of H, C$_1$–C$_8$ alkyl, C$_1$–C$_8$ fluoroalkyl, C$_1$–C$_8$ alkoxyl, C$_6$–C$_{10}$ cycloalkyl, C$_6$–C$_{10}$ aryl, C$_6$–C$_{10}$ fluoroaryl, C$_2$–C$_6$ vinyl, C$_3$–C$_6$ allyl, and oxiranylalkylene of formula (IV)

(IV)

wherein s is 0 or 1; and
y is an integer having a value of from 0 to 4 inclusive.

Preferably, the number of methylene groups, i.e., —(CH$_2$)— groups, in the silane compound of formula (III) is one or two.

The precursors of formula (III) employ bridged carbons between silicon atoms in the molecule, to improve film hardness. During deposition, the —(CH$_2$)$_x$— moieties remain in the film's cross-linking silicon centers, to provide significantly improved hardness, and concurrently lower k values due to the incorporation of carbon in the deposited film, in relation to corresponding silane precursors lacking the —(CH$_2$)$_x$— moieties of the formula (III) compounds.

The bridged silanes of formula (III) can be readily synthesized by derivatization of commercially available bridged chlorosilanes.

For example, Me(MeO)$_2$SiCH$_2$CH$_2$SiMe(OMe)$_2$ and Me$_2$(MeO)SiCH$_2$CH$_2$SiMe$_2$(OMe) are readily synthesized at yields of 82% and 88%, respectively, by the respective Reactions (4) and (5) set out below.

MeCl$_2$SiCH$_2$CH$_2$SiMeCl$_2$+4MeONa→Me(MeO)$_2$
SiCH$_2$CH$_2$SiMe(OMe)$_2$+4NaCl     Reaction (4)

Me$_2$ClSiCH$_2$CH$_2$SiMe$_2$Cl+2MeONa→Me$_2$(MeO)
SiCH$_2$CH$_2$SiMe$_2$(OMe)+2NaCl     Reaction (5)

(MeO)$_3$SiCH$_2$Si(OMe)$_3$ is correspondingly synthesized using MeONa by the reaction scheme of Reaction (6) set out below.

HSiCl$_2$CH$_2$HSiCl$_2$+4MeONa+2MeOH→(MeO)$_3$
SiCH$_2$Si(OMe)$_3$+4NaCl+2H$_2$     Reaction (6)

The compounds of formula (III) can be used as precursors for formation of low k, high strength films, in vapor deposition processes.

Such precursors of formula (III) can be employed alone or alternatively in combination with porogen materials, such as porogens of the formula (X):

$$R^{10}R^{11}SiR^{12}R^{13} \qquad (X)$$

wherein:
each of $R^{10}$, $R^{11}$, $R^{12}$ and $R^{13}$ can be the same as or different from one another and each is independently selected from the group consisting of H, C$_1$–C$_8$ alkyl, C$_1$–C$_8$ alkoxyl, C$_6$–C$_{10}$ cycloalkyl, and C$_6$–C$_{10}$ aryl, with the proviso that at least one of $R^{10}$, $R^{11}$, $R^{12}$ and $R^{13}$ is C$_1$–C$_8$ alkoxyl.
Preferred porogens include:

$^{t}Bu_2Si(OCH_3)_2$
$^{t}Bu_2Si(OC_2H_5)_2$
$(C_6H_5)_2Si(OCH_3)_2$
$(C_6H_5)_2Si(OC_2H_5)_2$
$(C_6H_{11})_2Si(OCH_3)_2$
$(C_6H_{11})_2Si(OC_2H_5)_2$
$^{t}BuSi(OCH_3)_2H$
$^{t}BuSi(OC_2H_5)_2H$
$(C_6H_5)Si(OCH_3)_2H$
$(C_6H_5)Si(OC_2H_5)_2H$
$(C_6H_{11})Si(OCH_3)_2H$
$(C_6H_{11})Si(OC_2H_5)_2H$
$(^{t}Bu)(CH_3)Si(OCH_3)_2$
$(^{t}Bu)(CH_3)Si(OC_2H_5)_2$
$(C_6H_5)(CH_3)Si(OCH_3)_2$
$(C_6H_5)(CH_3)Si(OC_2H_5)_2$
$(C_6H_{11})(CH_3)Si(OCH_3)_2$
$(C_6H_{11})(CH_3)Si(OC_2H_5)_2$
and the like, wherein $^{t}Bu$ is tertiary butyl.

It is also within the purview of the present invention to employ the organosilicon precursors of the invention, e.g., of Formula (I) and/or Formula (III), in combination with other organosilicon precursor compounds, such as TMCTS or other, e.g., cyclosiloxane, precursor(s), to provide improvement in the film properties that would otherwise be obtained using such other organosilicon precursor compounds in the absence of the organosilicon precursors of the invention.

It will be appreciated that the foregoing is illustrative of a wide variety of oxiranylsilane compounds and bridged silane compounds that can be synthesized within the general scope of the present invention and usefully employed to form low k, high strength films by vapor deposition methods.

The features and advantages of the invention are more fully shown with reference to the following non-limiting examples.

EXAMPLE 1

Synthesis of $Me(EtO_2)SiCHCH_2O$ m-CPBA (14 g, 62.47 mmol based on 77% purity) was dried in vacuum until vacuum reached 10 mTorr. Anhydrous methylene chloride (100 mL) was added to dissolve m-CPBA. $Me(EtO)_2SiCH=CH_2$ (10 g, 62.5 mmol) was added to the clear solution of m-CPBA in $CH_2Cl_2$. No visual changes immediately occurred. The white precipitate of m-$ClC_6H_4COOH$ formed within 2 hours. The reaction mixture was reduced in volume under vacuum (about 75 mL of $CH_2Cl_2$ were removed). Pentane (50 mL) was added and then the mixture was filtered. Low boiling point volatiles were removed in vacuum. The mixture of unreacted $Me(EtO)_2SiCH=CH_2$ (10%) and the product (90%) was isolated under vacuum distillation. Second distillation yielded high purity oxirane. Yield: 50%. Boiling point: 30° C. at 0.2 Torr. Mass spectrum: (EI, %): m/z 176 ($M^+$, 1), 161 ($M^+$-Me, 10), 133 ($M^+$-$CHCH_2O$, 100). $^1H$ NMR ($C_6D_6$): δ 3.76–3.64 (m, 4H, $SiOCH_2CH_3$), 2.59–2.5 (m, 2H, SiCHC$H_2$), 2.08–2.05 (m, 1H, $SiCHCH_2$), 1.17–1.07 (m, 6H, $SiOCH_2CH_3$), 0.07 (s, 3H, $SiCH_3$). $^{13}C$ NMR: ($C_6D_6$) δ 59.15 ($SiOCH_2CH_3$), 44.07 ($SiCHCH_2$), 18.91 ($SiOCH_2CH_3$), –6.25 ($SiCH_3$).

EXAMPLE 2

Synthesis of $Me(MeO)_2SiCH_2CHCH_2O$ m-CPBA (7.66 g, 34.18 mmol based on 77% purity) was dried in vacuum at room temperature until vacuum reached 10 mTorr. Anhydrous methylene chloride (60 mL) was added to dissolve m-CPBA. $Me(MeO)_2SiCH_2CH=CH_2$ (5 g, 34.18 mmol) was added to the solution of m-CPBA in $CH_2Cl_2$. The immediate reaction was evidenced by moderate heat generation. White precipitate of m-$ClC_6H_4COOH$ formed within 1 hour. The reaction mixture was left overnight. Next morning, the reaction mixture was reduced in volume under vacuum. Pentane (50 mL) was added and then the mixture was filtered. Low boiling point volatiles were removed in vacuum. The product was obtained by vacuum distillation. Yield: 40%. Boiling point 30° C. at 0.2 Torr. Mass spectrum: (EI, %): m/z 162 ($M^+$, 1), 174 ($M^+$-Me, 10), 105 ($M^+$-$CH_2CHCH_2O$, 100). 1H NMR ($C_6D_6$): δ 3.31 (s, 3H, $SiOCH_3$), 3.30 (s, 3H, $SiOCH_3$), 2.9–2.82 (m, 1H, $SiCH_2CHCH_2O$), 2.44–2.41 (m, 1H, $SiCH_2CHCHHO$), 2.18–2.15 (m, 1H, $SiCH_2CHCHHO$), 1.09–1.02 (m, 1H, $SiCHHCHCH_2O$), 0.73–0.65 (m, 1H $SiCHHCHCH_2O$), 0.08 (s, 3H, $SiCH_3$). $^{13}C$ NMR: ($C_6D_6$) δ 50.30 ($SiOCH_3$), 50.28 ($SiOCH_3$), 48.94 ($SiCH_2CHCH_2O$), 48.36 ($SiCH_2CHCH_2O$), 18.83 ($SiCH_2CHCH_2O$), –4.30 ($SiCH_3$).

EXAMPLE 3

Synthesis of $Me_2Si(CHCH_2O)_2$ m-CPBA (8 g, 35.70 mmol based on 77% purity) was dried in vacuum until vacuum reached 10 mTorr. Anhydrous methylene chloride (100 mL) was added to dissolve m-CPBA. The solution of $Me_2Si(CH=CH_2)_2$ (2 g, 17.86 mmol) in $CH_2Cl_2$ was added to the clear solution of m-CPBA in $CH_2Cl_2$. No visual changes occurred. The reaction mixture was left stirring overnight. White precipitate of m-$ClC_6H_4COOH$ formed by next morning. The mixture was reduced in volume under vacuum (about 80 mL of $CH_2Cl_2$ were removed). Pentane (50 mL) was added and then the mixture was filtered. Low boiling point volatiles were removed in vacuum. The mixture of $Me_2Si(CH=CH_2)(CHCH_2O)$ (15%) and the product (85%) was isolated using nitrogen trap under high vacuum. Yield: 50%. Boiling point: 45° C. at 0.2 Torr. Mass spectrum: (EI, %): m/z 101 ($M^{+-}CHCH_2O$, 20), 59 ($Me_2SiH$, 100). $^1H$ NMR ($C_6D_6$): δ 2.58–2.54 (m, 2H, $SiCHCHHO$), 2.38–2.28 (m, 2H, $SiCHCHHO$), 2.04–1.98 (m, 2H, $SiCHH_2O$), –0.10 and –0.12 (m, 6H, $SiCH_3$). $^{13}C$ NMR: ($C_6D_6$). δ 44.27 and 44.19 ($SiCHCH_2O$), 41.70 and 41.43 ($SiCHCH_2O$), –7.36, –7.50 and –7.74 ($SiCH_3$). The complicate NMR spectra are consistent with four stereoisomerisms possible for $Me_2Si(C*HCH_2O)_2$. Two diastereomers in the ratio of 1:1 were separated by GC/MS.

EXAMPLE 4

Synthesis of $[Me(MeO)_2SiCH_2]_2$

A solution of $[MeCl_2SiCH_2]_2$ (102.7 g, 0.4 mol) in tetrahydrofuran (THF) (500 mL) was added dropwise to 25 weight % solution of MeONa in MeOH (349 g, 1.6 mol, 1% excess) at room temperature. White precipitate formed almost immediately. The reaction mixture was stirred for 1 hour to ensure the complete substitution. Upon filtration, all volatiles were removed in vacuum to form a yellowish solution of MeONa in [Me(MeO)$_2$SiCH$_2$]$_2$. Pure [Me(MeO)$_2$SiCH$_2$]$_2$ was obtained by vacuum distillation. Yield: 82%. Boiling point: 55° C. at 0.3 Torr. Mass spectrum: (EI, %): m/z 238 (M$^+$, 5), 223 (M$^+$-Me, 15). $^1$H NMR (C$_6$D$_6$): δ 3.37 (s, 12H, OC$\underline{H}_3$), 0.72 (s, 4H, $\underline{H}_2$C—C$\underline{H}_2$), 0.09 (s, 6H, SiC$\underline{H}_3$). $^{13}$C NMR: (C$_6$D$_6$) δ 50.30 (O$\underline{C}$H$_3$), 4.98 (H$_2\underline{C}$—$\underline{C}$H$_2$), −5.99 (Si$\underline{C}$H$_3$).

EXAMPLE 5

Synthesis of [Me$_2$(MeO)SiCH$_2$]$_2$

A solution of [Me$_2$ClSiCH$_2$]$_2$ (100 g, 0.465 mol) in tetrahydrofuran (THF) (500 mL) was added dropwise to 25 weight % solution of MeONa in MeOH (200.68 g, 0.929 mol) at room temperature. White precipitate formed almost immediately. The reaction mixture was stirred for 1 hour to ensure the complete substitution. Upon filtration, all volatiles were removed in vacuum. Pure [Me$_2$(MeO)SiCH$_2$]$_2$ was obtained by vacuum distillation. Yield: 88%. Boiling point: 40° C. at 0.3 Torr. Mass spectrum: (EI, %): m/z 206 (M$^+$, 5), 191 (M$^+$-Me, 20), 89 (Me$_2$SiOMe, 100). $^1$H NMR (C$_6$D$_6$): δ 3.29 (s, 6H, OC$\underline{H}_3$), 0.59 (s, 4H, $\underline{H}_2$C—C$\underline{H}_2$), 0.09 (s, 6H, SiC$\underline{H}_3$). $^{13}$C NMR: (C$_6$D$_6$) δ 50.41 (O$\underline{C}$H$_3$), 7.92 (H$_2\underline{C}$—$\underline{C}$H$_2$), −2.76 (Si$\underline{C}$H$_3$).

EXAMPLE 6

Synthesis of [(MeO)$_3$Si]$_2$CH$_2$

A solution of (Cl$_2$ $_{HSi})_2$CH$_2$ (23.21 g, 0.108 mol) in tetrahydrofuran (THF) (120 mL) was added dropwise to 25 weight % solution of MeONa in MeOH (93.71 g, 0.434 mol) at room temperature. White precipitate formed almost immediately. The reaction mixture was stirred for 1 hour to ensure the complete substitution. Upon filtration, all volatiles were removed in vacuum and the product was obtained by vacuum distillation. Yield: 60%. Boiling point: 53° C. at 60 mTorr. Mass spectrum: (EI, %): m/z 256 (M$^+$, 20), 241 (M$^+$-Me, 5), 224 [M$^+$-OMe, 100]. $^1$H NMR (C$_6$D$_6$): δ 3.49 (s, 18H, OC$\underline{H}_3$), 0.08 (s, 2H, C$\underline{H}_2$). $^{13}$C NMR: (C$_6$D$_6$) δ 50.69 (O$\underline{C}$H$_3$), −9.02 ($\underline{C}$H$_2$).

EXAMPLE 7

Films Produced with diethoxy methyl oxiranyl silane (DEOMORS)

Me(EtO$_2$)SiCHCH$_2$O was synthesized as in Example 1.
The Me(EtO$_2$)SiCHCH$_2$O was employed to form a deposited film on a substrate by low pressure plasma-enhanced chemical vapor deposition, in which the deposition process was carried out under the process conditions listed in Table 1 below. The process was carried out in a deposition chamber to which vapor was introduced by a showerhead injection device to the wafer disposed on the wafer heater.

TABLE 1

| Deposition Parameter | Value |
| --- | --- |
| Syringe setpoint, % | 20 |
| Liquid flow, milliliters per minute | 0.13 |
| Substrate temperature, ° C. | 370 |
| Radio frequency power, watts | 250 |
| Pressure, torr | 6.0 |
| Spacing (showerhead to wafer heater distance), mils | 460 |

TABLE 1-continued

| Deposition Parameter | Value |
| --- | --- |
| Time, seconds | 120 |
| Carrier gas flow rate, sccm/minute | 200 |
| Carrier gas | carbon dioxide |

The deposited film had the characteristics shown in Table 2 below.

TABLE 2

| Film property | Value |
| --- | --- |
| Dielectric constant, k | 3.1 |
| Indentation hardness, GigaPascals (GPa) | 2.3 |
| Indentation modulus, GigaPascals (GPa) | 12.4 |
| Deposition Rate, Angstroms/min | 980 |

The film thus possessed an exceptional film hardness of 2.3 GPa with a dielectric constant k of 3.1. The film had less Si—H incorporation compared to films produced using precursors with large amounts of hydride, such as trimethylsilane and TMCTS. This is evidenced by the results in FIG. 1, which shows FTIR transmission spectra of a film deposited from TMCTS and a film deposited from Me(EtO$_2$) SiCHCH$_2$O under low oxygen activity deposition conditions. The presence of large amounts of Si—H in the film is generally correlated with reduced mechanical strength in low k films, and the low Si—H content of the film deposited from Me(EtO$_2$)SiCHCH$_2$O is consistent with the improvement achieved with the oxiranylsilane precursors of the present invention.

Films formed from oxiranylsilane precursors also demonstrate compatibility with low oxygen activity plasmas, which render such precursors compatible with oxygen sensitive porogens, e.g., organosilicon precursors containing t-butyl functional groups. The process conditions summarized in Table 1 reflect the fact that a small amount of CO$_2$ and the Me(EtO$_2$)SiCHCH$_2$O precursor were the only potential sources of oxygen in the plasma. Under conditions similar to this, many hydride-containing precursors such as TMCTS show a severely depressed deposition rate, and poor dielectric constant and hardness characteristics. Large amounts of Si—H are observed in films deposited from TMCTS. Si—H is not detected in films deposited under similar conditions using Me(EtO$_2$)SiCHCH$_2$O.

Figure 2:
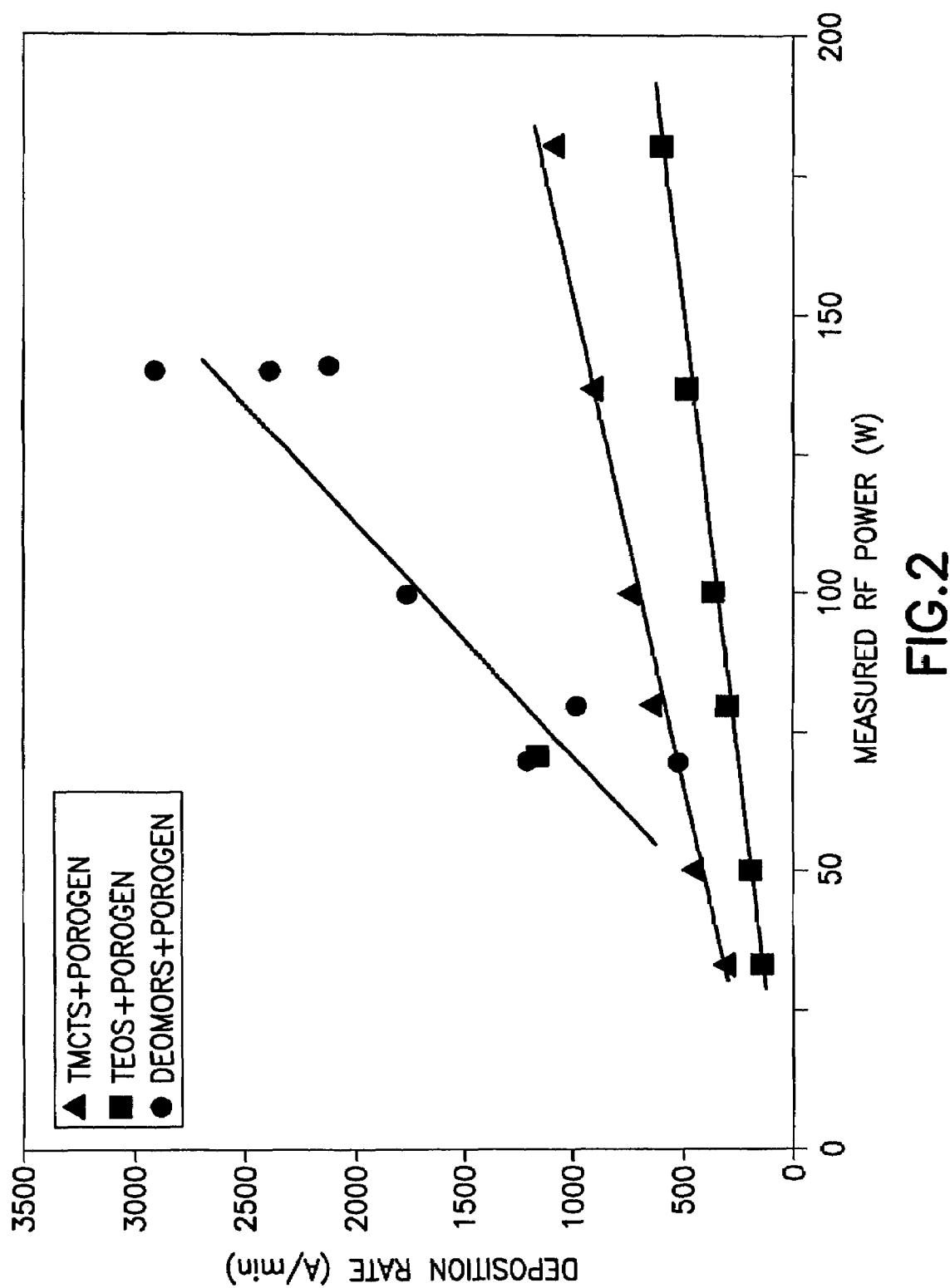
FIG. 2 is a plot of deposition rate, in Angstroms per minute, as a function of measured radio frequency power, in watts, for each of Me(EtO$_2$)SiCHCH$_2$O (denoted in the graph as DEOMORS), tetramethylcyclotetrasiloxane (denoted in the graph as TMCTS), and tetraethylorthosilicate (denoted in the graph as TEOS), each utilized in the deposition process in combination with a same porogen under similar conditions.

FIG. 2 is a plot of deposition rate, in Angstroms per minute, as a function of measured radio frequency power, in watts, for each of Me(EtO$_2$)SiCHCH$_2$O (denoted in the graph as DEOMORS), tetramethylcyclotetrasiloxane (denoted in the graph as TMCTS), and tetraethylorthosilicate (denoted in the graph as TEOS), each utilized in the deposition process in combination with a same porogen under similar conditions.

As shown by the results of FIG. 2, Me(EtO$_2$)SiCHCH$_2$O evidenced a markedly higher deposition rate in comparison with the prior art TEOS and TMCTS precursor materials.

Although the invention has been variously disclosed herein with reference to illustrative embodiments and features, it will be appreciated that the embodiments and features described hereinabove are not intended to limit the invention, and that other variations, modifications and other embodiments will suggest themselves to those of ordinary skill in the art. The invention therefore is to be broadly construed, consistent with the claims hereafter set forth.

The invention claimed is:

1. An organosilicon precursor for vapor deposition of a low k, high strength dielectric film, wherein the precursor comprises at least one silicon-pendant oxiranyl functionality and is selected from the group consisting of compounds of Formula (A) and Formula (B):

Formula (A), Me(EtO)$_2$SiCHCH$_2$O:

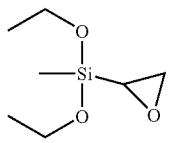

Formula (B), Me(MeO)$_2$SiCH$_2$CHCH$_2$O:

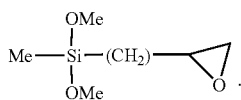

2. The organosilicon precursor of claim 1, having Formula (A).

3. The organosilicon precursor of claim 1, having Formula (B).

4. The organosilicon precursor of claim 1, wherein the precursor further comprises TMCTS.

5. An organosilicon precursor composition for vapor deposition of a low k, high strength dielectric film, wherein the composition comprises:
(A) an organosilicon precursor comprising at least one silicon-pendant oxiranyl functionality, wherein said organosilicon precursor is selected from the group consisting of compounds of Formula (A) and Formula (B):

Formula (A), Me(EtO)$_2$SiCHCH$_2$O:

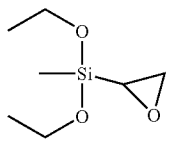

Formula (B), Me(MeO)$_2$SiCH$_2$CHCH$_2$O:

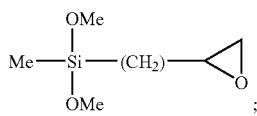;

(B) a porogen.

6. The organosilicon precursor composition of claim 5, wherein said porogen is selected from the group consisting of compounds of the formula (X):

$$R^{10}R^{11}Si\ R^{12}R^{13} \qquad (X)$$

wherein:
each of $R^{10}$, $R^{11}$, $R^{12}$ and $R^{13}$ can be the same as or different from one another and each is independently selected from the group consisting of H, $C_1$–$C_8$ alkyl, $C_1$–$C_8$ alkoxyl, $C_6$–$C_{10}$ cycloalkyl, and $C_6$–$C_{10}$ aryl, with the proviso that at least one of $R^{10}$, $R^{11}$, $R^{12}$ and $R^{13}$ is $C_1$–$C_8$ alkoxyl.

7. The organosilicon precursor composition of claim 5, wherein said porogen is selected from the group consisting of:
$^tBu_2Si(OCH_3)_2$
$^tBu_2Si(OC_2H_5)_2$
$(C_6H_5)_2Si(OCH_3)_2$
$(C_6H_5)_2Si(OC_2H_5)_2$
$(C_6H_{11})_2Si(OCH_3)_2$
$(C_6H_{11})_2Si(OC_2H_5)_2$
$^tBuSi(OCH_3)_2H$
$^tBuSi(OC_2H_5)_2H$
$(C_6H_5)Si(OCH_3)_2H$
$(C_6H_5)Si(OC_2H_5)_2H$
$(C_6H_{11})Si(OCH_3)_2H$
$(C_6H_{11})Si(OC_2H_5)_2H$
$(^tBu)(CH_3)Si(OCH_3)_2$
$(^tBu)(CH_3)Si(OC_2H_5)_2$
$(C_6H_5)(CH_3)Si(OCH_3)_2$
$(C_6H_5)(CH_3)Si(OC_2H_5)_2$
$(C_6H_{11})(CH_3)Si(OCH_3)_2$
$(C_6H_{11})(CH_3)Si(OC_2H_5)_2$
wherein $^tBu$ is tertiary butyl.

8. A method of forming an oxiranylsilane compound selected from the group consisting of comuounds of Formula (A) and Formula (B):

Formula (A), Me(EtO)$_2$SiCHCH$_2$O:

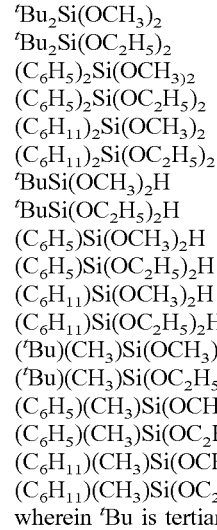

Formula (B), Me(MeO)$_2$SiCH$_2$CHCH$_2$O:

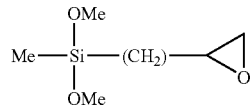

said method comprising oxidizing a corresponding vinylsilane or allylsilane compound.

9. The method of claim 8, wherein the step of oxidizing comprises reaction with an oxidizing agent that is inert in relation to Si—OR fragments.

10. The method of claim 9, wherein said oxidizing agent comprises an agent selected from the group consisting of meta-Cl(C$_6$H$_4$)C(O)OOH, $^tBuOOH$, wherein $^tBu$ is tertiary butyl, and Me$_3$SiOOSiMe$_3$, wherein Me is methyl.

11. The method of claim 9, wherein said oxidizing agent comprises meta-Cl(C$_6$H$_4$)C(O)OOH.

12. The method of claim 8, wherein said step of oxidizing is conducted in a non-flammable solvent medium.

13. The method of claim 12, wherein said non-flammable solvent medium comprises dichloromethane.

14. The method of claim 12, wherein said non-flammable solvent medium comprises chloroform.

15. The method of claim 8, wherein said oxiranylsilane compound is Me(EtO)$_2$SiCHCH$_2$O.

16. The method of claim 8, wherein said oxiranylsilane is Me(MeO)$_2$SiCH$_2$CHCH$_2$O.

17. A method of forming a low k, high strength dielectric film on a substrate, comprising vapor depositing said film on the substrate from an organosilicon precursor, wherein said precursor comprises at least one silicon-pendant oxiranyl functionality and is selected from the group consisting of compounds of Formula (A) and Formula (B):

Formula (A), Me(EtO)$_2$SiCHCH$_2$O:

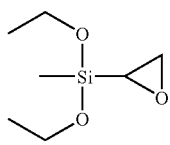

Formula (B), Me(MeO)$_2$Si CH$_2$CHCH$_2$O:

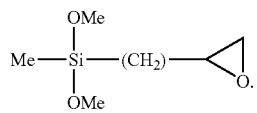

18. The method of claim 17, wherein the precursor comprises a compound of Formula (A).

19. The method of claim 17, wherein the precursor comprises a compound of Formula (B).

20. The method of claim 17, wherein said vapor depositing step comprises use of a porogen in combination with said precursor.

21. The method of claim 20, wherein said porogen is selected from the group consisting of compounds of the formula (X):

$$R^{10}R^{11}R^{12}R^{13} \quad (X)$$

wherein:
each of $R^{10}$, $R^{11}$, $R^{12}$ and $R^{13}$ can be the same as or different from one another and each is independently selected from the group consisting of H, C$_1$–C$_8$ alkyl, C$_1$–C$_8$ alkoxyl, C$_6$–C$_{10}$ cycloalkyl, and C$_6$–C$_{10}$ aryl, with the proviso that at least one of $R^{10}$, $R^{11}$, $R^{12}$ and $R^{13}$ is C$_1$–C$_8$ alkoxyl.

22. The method of claim 20, wherein said porogen is selected from the group consisting of:
$^t$Bu$_2$Si(OCH$_3$)$_2$
$^t$Bu$_2$Si(OC$_2$H$_5$)$_2$
(C$_6$H$_5$)$_2$Si(OCH$_3$)$_2$
(C$_6$H$_5$)$_2$Si(OC$_2$H$_5$)$_2$
(C$_6$H$_{11}$)$_2$Si(OCH$_3$)$_2$
(C$_6$H$_{11}$)$_2$Si(OC$_2$H$_5$)$_2$
$^t$BuSi(OCH$_3$)$_2$H
$^t$BuSi(OC$_2$H$_5$)$_2$H
(C$_6$H$_5$)Si(OCH$_3$)$_2$H
(C$_6$H$_5$)Si(OC$_2$H$_5$)$_2$H
(C$_6$H$_{11}$)Si(OCH$_3$)$_2$H
(C$_6$H$_{11}$)Si(OC$_2$H$_5$)$_2$H
($^t$Bu)(CH$_3$)Si(OCH$_3$)$_2$
($^t$Bu)(CH$_3$)Si(OC$_2$H$_5$)$_2$
(C$_6$H$_5$)(CH$_3$)Si(OCH$_3$)$_2$
(C$_6$H$_5$)(CH$_3$)Si(OC$_2$H$_5$)$_2$
(C$_6$H$_{11}$)(CH$_3$)Si(OCH$_3$)$_2$
(C$_6$H$_{11}$)(CH$_3$)Si(OC$_2$H$_5$)$_2$
wherein $^t$Bu is tertiary butyl.

23. The method of claim 17, wherein said vapor depositing step comprises chemical vapor deposition.

24. The method of claim 17, wherein said vapor depositing step comprises plasma-enhanced chemical vapor deposition.

25. The method of cliam 17, wherein said vapor depositing step comprises flowing said precursor to a vapor deposition locus in a carrier gas.

26. The method of cliam 25, wherein said carrier gas comprises carbon dioxide.

27. The method of cliam 25, wherein the precursor and the carrier gas are the only potential sources of oxygen at the vapor deposition locus.

28. The method of cliam 17, wherein the precursor is selected from the group consisting of:
Me(EtO)$_2$SiCHCH$_2$O; and
Me(MeO)$_2$SiCH$_2$CHCH$_2$O.

29. The method of cliam 17, wherein the precursor further comprises TMCTS.

* * * * *